United States Patent [19]

Bugaut et al.

[11] Patent Number: 4,702,863
[45] Date of Patent: Oct. 27, 1987

[54] INDOANILINE AND INDOPHENOL COMPOUNDS, A PROCESS FOR THEIR PREPARATION, DYEING COMPOSITIONS CONTAINING THEM AND A HAIR-DYEING PROCESS

[75] Inventors: Andrée Bugaut, Boulogne; Alex M. Junino, Aulnay, both of France

[73] Assignee: L'Oreal, Paris, France

[21] Appl. No.: 884,904

[22] Filed: Jul. 14, 1986

Related U.S. Application Data

[63] Continuation of Ser. No. 618,336, Jun. 7, 1984.

[30] Foreign Application Priority Data

Jun. 13, 1983 [FR] France ............................. 83 09735

[51] Int. Cl.⁴ ..................... C07C 50/04; C07C 50/06
[52] U.S. Cl. .............................................. 260/396 N
[58] Field of Search ................................ 260/396 N

[56] References Cited

U.S. PATENT DOCUMENTS

| | | | |
|---|---|---|---|
| 3,834,866 | 9/1974 | Pum et al. ................................ | 8/11 |
| 3,905,761 | 9/1975 | Kalopissis et al. ............ | 260/396 N |
| 4,246,181 | 1/1981 | Kalopissis et al. ............ | 260/396 N |

FOREIGN PATENT DOCUMENTS

| | | | |
|---|---|---|---|
| 2359182 | 2/1978 | France ........................... | 260/396 N |
| 2142920A | 1/1985 | United Kingdom ........... | 260/396 N |

OTHER PUBLICATIONS

*Chemical Abstract*, vol. 89, Grollier, 1/26/78 (Abstract of related French Patent No. 2,359,182 above).
*Chemical Abstract*, vol. 95, Matsuki et al, 1981, Characterization of Amino-indomine and Aminoaniline Formed by Oxidative Hair Drying and their Mutagenicity.
Abarhart, *Dyes and Their Intermediates*, 1968, p. 8.

*Primary Examiner*—Glennon H. Hollrah
*Assistant Examiner*—Raymond Covington
*Attorney, Agent, or Firm*—Cushman, Darby & Cushman

[57] ABSTRACT

New indolaniline and indophenol compounds of formula (I):

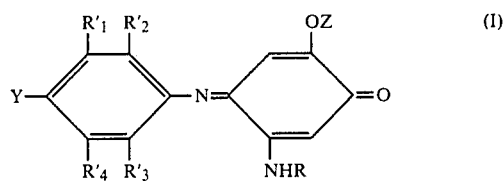

wherein Z represents a monohydroxylated or polyhydroxylated hydrocarbon radical, of 1 to 6 carbon atoms, or an aminoalkyl radical of formula

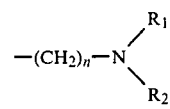

wherein n is an integer from 1 to 6 and $R_1$ and $R_2$, which are identical or different, represent a hydrogen atom or an alkyl, hydroxyalkyl or acyl radical of 1 to 4 carbon atoms; R represents a hydrogen atom or an alkyl, hydroxyalkyl, polyhydroxyalkyl, monocarbamylalkyl, dicarbamylalkyl, aminoalkyl, acyl, alkoxycarbonyl, carbamyl or monoalkylcarbamyl radical of 1 to 6 carbon atoms; $R'_1$, $R'_2$, $R'_3$ and $R'_4$, which are identical or different, represent a hydrogen atom, a halogen atom or an alkyl, hydroxyalkyl, alkoxy or hydroxyalkoxy radical, of 1 to 6 carbon atoms; and Y represents OH or $NR'_5R'_6$, wherein $R'_5$ and $R'_6$, which are identical or different, represent a hydrogen atom or an alkyl, monohydroxyalkyl, polyhydroxyalkyl, carbamylalkyl, mesylaminoalkyl or methoxy alkyl radical of 1 to 6 carbon atoms are disclosed, together with a process for their preparation, hair-dyeing compositions containing them and a hair dyeing process.

13 Claims, No Drawings

INDOANILINE AND INDOPHENOL COMPOUNDS, A PROCESS FOR THEIR PREPARATION, DYEING COMPOSITIONS CONTAINING THEM AND A HAIR-DYEING PROCESS

This is a continuation of application Ser. No. 618,336, filed June 7, 1984.

The present invention relates to new indoaniline and indophenol compounds, compositions containing them, a process for their preparation and their use in dyeing hair.

The object of the invention is to provide new chemical compounds which can advantageously be employed as direct colorants for hair-dyeing, that is to say capable, depending on the nature of the substitutions in the molecule, of imparting to hair a whole range of colours which are fairly intense and stable to light, inclement weather and washing. The compounds should also possess the advantage of being substantially innocuous, in particular insofar as the mutagenic potential is concerned.

The present invention provides compounds of formula (I)

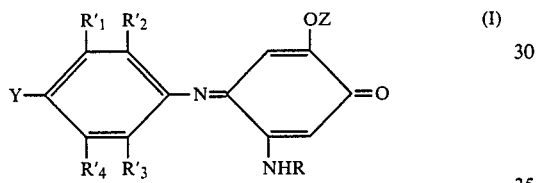

wherein Z represents a monohydroxylated or polyhydroxylated hydrocarbon radical of 1 to 6 carbon atoms, or an aminoalkyl radical of formula

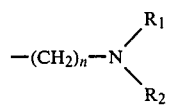

wherein n is an integer from 1 to 6 and $R_1$ and $R_2$, which are identical or different, represent a hydrogen atom or an alkyl, mono- or polyhydroxyalkyl, or acyl radical of 1 to 4 carbon atoms; R represents a hydrogen atom or an alkyl, hydroxyalkyl, polyhydroxyalkyl, monocarbamylalkyl, dicarbamylalkyl, aminoalkyl, acyl, alkoxycarbonyl, carbamyl or monoalkylcarbamyl radical, of 1 to 6 carbon atoms; $R'_1$, $R'_2$, $R'_3$ and $R'_4$, which are identical or different, represent a hydrogen atom, a halogen atom or an alkyl, hydroxyalkyl, alkoxy or hydroxyalkoxy radical, of 1 to 6 carbon atoms; and Y represents OH or $NR'_5R'_6$, wherein $R'_5$ and $R'_6$, which are identical or different, represent a hydrogen atom or an alkyl, monohydroxyalkyl, polyhydroxyalkyl, carbamylalkyl, mesylaminoalkyl or methoxyalkyl radical, of 1 to 6 carbon atoms.

When Z is a mono- or polyhydroxylated radical, it preferably represents a —CH$_2$CH$_2$OH, —CH$_2$—CHOH—CH$_2$OH or —CH$_2$—CHOH—CH$_3$ radical. When Z is an aminoalkyl radical, it preferably represents a —CH$_2$—CH$_2$NH$_2$, —CH$_2$—CH$_2$—NHCH$_3$, —CH$_2$—CH$_2$—NHCOCH$_3$ or

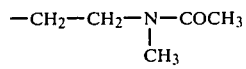

radical. When R is an acyl radical, it preferably represents a formyl, acetyl or propionyl radical. R also preferably represents a hydrogen atom.

The compounds of formula (I) may typically be obtained by reacting, in an oxidising alkaline medium, a para-phenylenediamine or a para-aminophenol of formula (II)

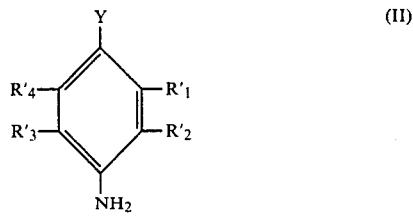

wherein Y, $R'_1$, $R'_2$, $R'_3$ and $R'_4$ are as defined above, with a meta-aminophenol of formula (III)

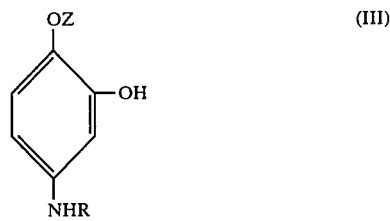

wherein R and Z are as defined above.

The compounds of formula (I), in which Y represents $NR'_5R'_6$, wherein $R'_5$ and $R'_6$ are as defined above, but may not both denote hydrogen, may also typically be obtained by reacting, in an alcoholic solution under reflux, a p-nitroso derivative of formula (IV)

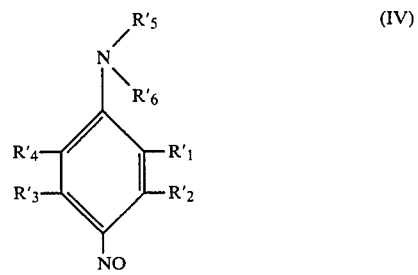

wherein $R'_1$, $R'_2$, $R'_3$, $R'_4$, $R'_5$ and $R'_6$ are as defined above, with a meta-aminophenol of formula (III).

When R represents an acyl radical, the compound of formula (I) may be subjected to an alkaline hydrolysis in order to convert R into a hydrogen atom.

A method of preparation of compounds of formula (III) is described in French patent application No. 8309734 (British patent application No. 2,142,920A) the disclosure of which is hereby incorporated by reference. This process comprises reacting, in the presence of a strong base, an alcohol with 3,4-methylenedioxy-1-nitrobenzene to obtain a nitro derivative, which is converted by reduction to the corresponding amine compound, the reduction being carried out, for example, with iron in an acetic acid medium or with cyclohexene in the presence of a palladium/charcoal catalyst. The alcohols which are used may contain an acylated amine group, in which case the meta-aminophenols obtained can be subjected to a hydrolysis using hydrochloric acid. The aromatic amine and/or the amine outside the ring in the meta-aminophenols obtained may also be substituted to obtain the desired compounds of formula (III).

Most of the direct colorants of formula (I) are more soluble in an aqueous-alcoholic medium than compounds of formula (V)

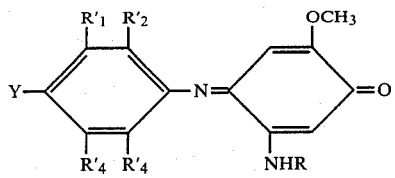

which may be obtained by reacting, in an oxidising alkaline medium, a para-phenylenediamine or a para-aminophenol of formula (II) with a coupler of formula (VI).

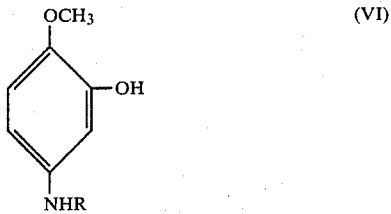

The coupler of formula (VI) is disclosed in U.S. Pat. No. 3,834,866, the disclosure of which is hereby incorporated by reference.

The table below illustrates, by way of examples, the differences in solubility at 25° C. in a mixture of 75% water and 25% ethanol between some compounds of formula (I) and corresponding compounds of formula (V), in which Z is replaced by $CH_3$.

| | | maximum solubility at 25° C. in a mixture of 75% water and 25% ethanol |
|---|---|---|
| R = H | $Z_1 = CH_3$ | 0.15% |
| | $Z_1 = Z = CH_2-CH_2OH$ | 0.41% |
| | $Z_1 = Z = CH_2-CHOH-CH_2OH$ | 0.84% |
| R = $COCH_3$ | $Z_1 = CH_3$ | 0.03% |
| | $Z_1 = Z = CH_2-CH_2OH$ | 0.2% |

This solubility increase due to the OZ group as defined in formula (I) allows colorants of formula (I) to be used in sufficiently high concentrations to produce colours of adequate intensity.

Compounds of formula (I) when used as hair dyes provide good stability to light, washing and inclement weather of the hair colour. This stability is most marked when R represents hydrogen or a substituted or unsubstituted alkyl radical.

Compounds of formula (I), in hair-dyeing, are substantially innocuous. More particularly, they have not been found to be mutagenic in the Ames test on Salmonella Typhimurium, with or without an $S_9$ mix activated with Arochlor. This property is surprising, since some compounds of formula (V), in which the OZ group in formula (I) is replaced by $OCH_3$, have been found to be highly mutagenic according to the same test. This is the case, for example, for [(4'-amino)phenyl]-2-amino-5-methoxy-1,4-benzoquinoneimine and [(4'-amino-3'-methyl)phenyl]-2-amino-5-methoxy-1,4-benzoquinoneimine, which have been found to be highly mutagenic, with or without an $S_9$ mix (Arochlor activation) to the strains $T_A100$, $T_A98$ and $T_A1538$. The highly mutagenic action of the latter compound is disclosed in Chemical Abstracts, Selects-Proton Magnetic Resonance, page 1, volume 18, 1981, number 95: 75096 f.

The present invention also provides a hair-dyeing composition comprising, in a cosmetic base, at least one compound of formula (I).

The dyeing composition according to the invention preferably contains from 0.01 to 2% by weight of a compound of formula (I) relative to the total weight of the composition.

The dyeing compositions according to the invention are typically solutions in aqueous alcohol; they may additionally include a cosmetic resin to form what is known as a colouring hair-setting lotion, the said lotion being capable of being applied to wet hair before setting.

The compounds of formula (I) may be used alone, in which case it is possible to obtain a range of colourings from yellow to a more or less orange yellow, from red to purple and from blue to blue-green.

They may also be used in a mixture, with other known indoanilines, indophenols or indamines, or with other direct colorants such as the direct nitro colorants of the benzene series, anthraquinone derivatives, azo derivatives or azomethines. Examples of these direct colorants are; 1-N,N-bis-($\beta$-hydroxyethyl)amino-3-nitro-4-N'-methylaminobenzene, 1-N,N-(methyl-$\beta$-hydroxyethyl)amino-3-nitro-4-N'-($\beta$-hydroxyethyl)aminobenzene, 5-nitro-4-N-($\beta$-hydroxyethyl)aminophenol, 2-N-($\beta$-hydroxyethyl)amino-5-nitroanisole, 1-amino-2-nitro-4-N-($\beta$-hydroxyethyl)amino-5-methylbenzene, N,N'-($\beta$-hydroxyethyl)-4-nitro-orthophenylenediamine, 3-nitro-4-N-($\beta$-aminoethyl)aminophenoxyethanol, 4-nitro-3-N-methylaminophenoxyethanol, 1-N-($\beta$-amino-ethyl)amino-2-nitro-4-N',N'-($\beta$-hydroxyethyl)aminobenzene, [3-nitro-4-N-($\beta$-hydroxyethyl)amino]phenyl 2',3'-dihydroxypropyl ether, 2-N-($\beta$-hydroxyethyl)amino-5-nitrophenol, 3-N-($\beta$-aminoethyl)amino-4-nitroanisole, 1-amino-2-nitro-4-N-(2',3'-dihydroxypropyl)amino-5-methylbenzene, [2-N-($\beta$-hydroxyethyl)amino-5-nitro]phenoxyethanol, 3-nitro-4-aminophenol, 2-methyl-4-amino-5-nitrophenol, (3-N-methylamino-4-nitro)phenyl 2',3'-dihydroxypropyl ether, 2-amino-3-nitrophenol, (3-N-methylamino-4-nitro)phenoxyethanol, 1,4,5,8-tetraaminoanthraquinone, or their salts.

The pH of the dyeing compositions according to the invention is preferably from 6 to 8.5. Alkalising agents which may be used are, for example, ammonia, alkylamines such as ethylamine or triethylamine, alkanolamines such as the mono-, di- or triethanolamine, alkylalkanolamines such as methyldiethanolamine, 2- amino-2-methylpropan-1-ol and 2-amino-2-methylpropane-1,3-diol, sodium or potassium hydroxide, or sodium, potassium or ammonium carbonate.

Compositions according to the invention may also contain thickening agents and be in the form of creams or gels. A distinction can be made between the direct dyes, in the case of which the compositions are more complex, and the hair-setting lotions which consist of simple solutions in aqueous alcohol containing a resin.

The compositions according to the invention may, in addition, contain various ingredients usually employed in cosmetics, for example solvents, surfactants, dispersing agents, swelling agents, penetrating agents, emollients or perfumes. They may, for example, be packaged in aerosol bottles.

The colouring hair-setting lotions according to the invention contain at least one compound of formula (I) typically in a quantity of 0.01 to 2% by weight and, preferably, 0.05 to 1% by weight, in an aqueous-alcohol vehicle typically containing 10 to 70% and, preferably, 20 to 50% by weight of an alcohol or alcohols, in the presence of a cosmetic polymer typically in a concentration of 0.5 to 4% and, preferably, 1 to 3% by weight. The aqueous alcoholic solution mainly contains lower alcohols preferably, ethanol or isopropanol.

Any cationic, anionic, non-ionic or amphoteric polymer usually employed in this type of composition may be used as a cosmetic resin, for example:
PVP K 30—polyvinylpyrrolidone (MW 40,000);
PVP K 60—polyvinylpyrrolidone (MW 160,000);
PVP K 90—polyvinylpyrrolidone (MW 360,000);
PVP/VA E 735—polyvinylpyrrolidone/vinyl acetate 70/30 (MW 40,000);
PVP/VA E 535—polyvinylpyrrolidone/vinyl acetate 50/50
PVP/VA E 335—polyvinylpyrrolidone/vinyl acetate 30/70 (MW 160,000);
PVP/VA S 630—polyvinylpyrrolidone/vinyl acetate 60/40
(viscosity determined at 25° C. for a 5% solution in ethanol: 3.3 to 4 cps), as well as the following resins for which the specific viscosity, measured for a 1% solution in methyl ethyl ketone at a temperature of 25° C., is shown:
methyl vinyl ether/maleic anhydride copolymers and, in particular, those known under the names "GANTREZ AN 119" (viscosity 0.1 to 0.5), "GANTREZ AN 139" (viscosity 1.0 to 1.4), "GANTREZ AN 149" (viscosity 1.5 to 2), "GANTREZ AN 169" (viscosity 2.6 to 3.5),
esters of methyl vinyl ether/maleic anhydride copolymers and, in particular, the resin "GANTREZ ES 225" (ethyl monoester of "GANTREZ AN 119"), "GANTREZ ES 335-I" (isopropyl monoester of "GANTREZ AN 119"), "GANTREZ ES 425" (butyl monoester of "GANTREZ AN 119") and "GANTREZ ES 435" (butyl monoester of "GANTREZ AN 119"),
copolymers based on crotonic acid and vinyl acetate such as the resin 28-1310 (MW 20,000), the resin 28-29-30 (intrinsic viscosity 0.32 in acetone at 30° C.),
the vinyl acetate/allyl stearate/allyloxyacetic acid terpolymer (80:15:5) (4.4 to 5 cps in a 5% solution in dimethylformamide at 35° C.),
"GAFQUAT 734" (quaternary copolymer of polyvinylpyrrolidone) (MW 100,000) and
methyl/stearyl/dimethylaminoethyl methacrylate terpolymers, completely quaternised with dimethyl sulphate (intrinsic viscosity 8 to 12 cps in 5% solution in dimethylformamide at 35° C.).

The present invention also provides a new process for dyeing hair wherein a dyeing composition as defined above is left to act on the hair for a period of application typically varying from 10 to 45 min and at a temperature of from 15° to 50° C. followed by rinsing, and, optionally, washing the hair and rinsing again and drying.

The present invention also provides a new process for setting hair, wherein a colouring hair-setting lotion containing at least one compound of formula (I) is applied, typically at a temperature of from 15° to 30° C., to wet hair, for example, after washing and rinsing it, and the hair is wound for setting and is then dried.

The direct dyes or colouring hair-setting lotions according to the invention may be applied to any kind of keratin fibres, but are preferably used on naturally white hair or hair which has been bleached first.

The invention will now be further described by means of the following examples.

All the meta-aminophenols of formula (III) employed as starting materials for the synthesis of indoanilines and indophenols of formula (I) which are described in the preparation examples which follow are described in the French Patent Application No. 8309734.

EXAMPLE 1

Preparation of
N-[(4'-amino)phenyl]-2-acetylamino-5-β-hydroxyethoxy-1,4-benzoquinoneimine

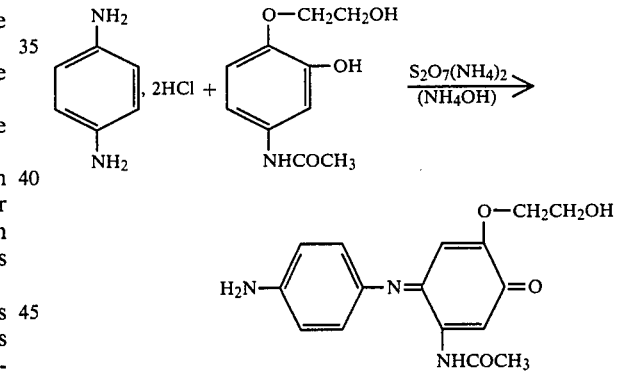

0.043 mole (9.2 g) of (2-hydroxy-4-acetylamino)-phenoxyethanol dissolved in 85 ml of isopropyl alcohol and 85 ml of 22°Bé strength ammonia is added, with effective stirring, to 260 g of crushed ice. 0.087 mole (19.8 g) of ammonium persulphate dissolved in 65 ml of water, and 0.0434 mole (7.9 g) of para-phenylenediamine dihydrochloride are added, simultaneously and gradually, between 0° and 5° C., while stirring is continued. When the expected indoaniline has precipitated, it is filtered, washed with water and then with a little acetone and is dried under vacuum. After being recrystallised from absolute ethanol and dried under vacuum at 80° C., the product melts at 192° C.

Analysis of the product obtained gives the following results:

| ANALYSIS | CALCULATED FOR $C_{16}H_{17}N_3O_4$ | FOUND |
|---|---|---|
| C % | 60.95 | 61.02 |

-continued

| ANALYSIS | CALCULATED FOR $C_{16}H_{17}N_3O_4$ | FOUND |
|---|---|---|
| H % | 5.40 | 5.28 |
| N % | 13.33 | 13.18 |
| O % | 20.32 | 20.21 |

EXAMPLE 2

Preparation of
N-[(4'-amino)phenyl]-2-amino-5-β-hydroxyethoxy-1,4-benzoquinoneimine

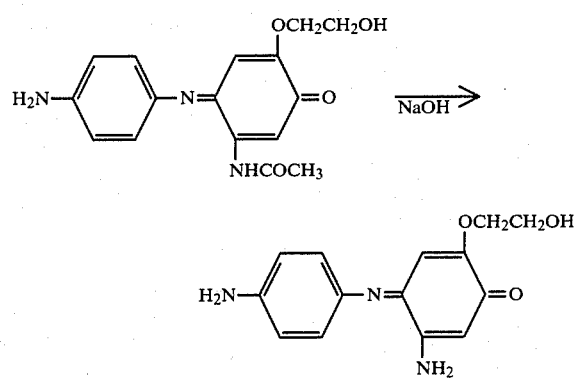

0.0138 mole (5 g) of the indoaniline obtained in Example 1 is suspended in 50 mL of a solution in aqueous alcohol (60% ethanol and 40% water). 50 ml of a normal soda solution are added, with stirring. The dissolution takes place immediately; after about 30 minutes, the deacetylation, which is followed by thin-layer chromatography, is complete; the new indoaniline precipitates in the form of bronze-coloured flakes. This indoaniline is filtered off, washed with water and recrystallised from ethanol. After drying under vacuum at 60° C., the product melts at 222° C.

Analysis of the product obtained gives the following results:

| ANALYSIS | CALCULATED FOR $C_{14}H_{15}N_3O_3$ | FOUND |
|---|---|---|
| C % | 61.54 | 61.29 |
| H % | 5.49 | 5.50 |
| N % | 15.38 | 15.28 |
| O % | 17.58 | 17.77 |

EXAMPLE 3

Preparation of
N-[(4'-amino)phenyl]-2-acetylamino-5-β,γ-dihydroxypropoxy-1,4-benzoquinoneimine

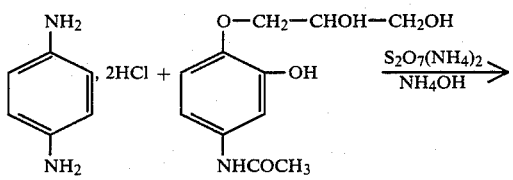

-continued

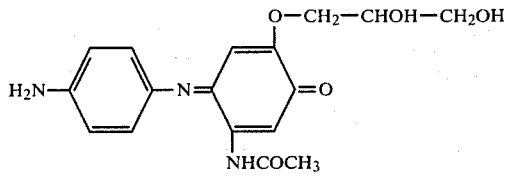

0.1 mole (24.1 g) of 1-(2-hydroxy-4-acetylaminophenoxy)propane-2,3-diol dissolved in 200 ml of isopropyl alcohol and 200 ml of 22°Bé strength ammonia is added, with effective stirring, to 750 g of crushed ice. 0.2 mole (45.6 g) of ammonium persulphate dissolved in 150 ml of water, and 0.1 mole (18.1 g) of paraphenylenediamine dihydrochloride dissolved in 150 ml of water are added, simultaneously and gradually over a period of 20 minutes, at a temperature close to 0° C. while stirring is continued. When the additions have been completed, the expected indoaniline, which has precipitated, is filtered off. It is washed with water and cold ethanol. After recrystallisation from ethanol and drying under vacuum at 70° C., the product melts at 220° C.

Analysis of the product obtained gives the following results:

| ANALYSIS | CALCULATED FOR $C_{17}H_{19}N_3O_5$ | FOUND |
|---|---|---|
| C % | 59.13 | 59.08 |
| H % | 5.51 | 5.46 |
| N % | 12.18 | 12.22 |
| O % | 23.15 | 23.13 |

EXAMPLE 4

Preparation of
N-[(4'-amino)phenyl]-2-amino-5-β,γ-dihydroxypropoxy-1,4-benzoquinoneimine

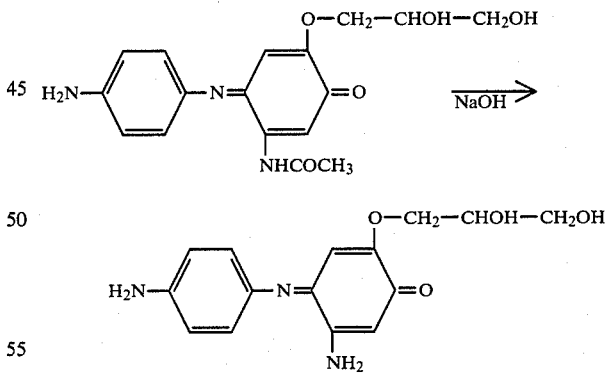

0.017 mole (6 g) of the indoaniline obtained on Example 3 is suspended in 50 ml of an aqueous alcohol solution (60% of ethanol, 40% of water). 60 ml of 0.5N soda solution are added, with stirring. The mixture very rapidly becomes homogeneous and then the expected indoaniline precipitates. After 45 minutes it is filtered off, washed with water and recrystallised from dimethyl sulphoxide. After drying under vacuum at 70° C., the product melts at 182° C.

Analysis of the product obtained gives the following results:

| ANALYSIS | CALCULATED FOR $C_{15}H_{17}N_3O_4$ | FOUND |
|---|---|---|
| C % | 59.40 | 59.29 |
| H % | 5.61 | 5.66 |
| N % | 13.86 | 13.85 |
| O % | 21.12 | 21.22 |

EXAMPLE 5

Preparation of
N-[(4'-hydroxy-2'-chloro)phenyl]-2-acetylamino-5-β-hydroxyethoxy-1,4-benzoquinoneimine

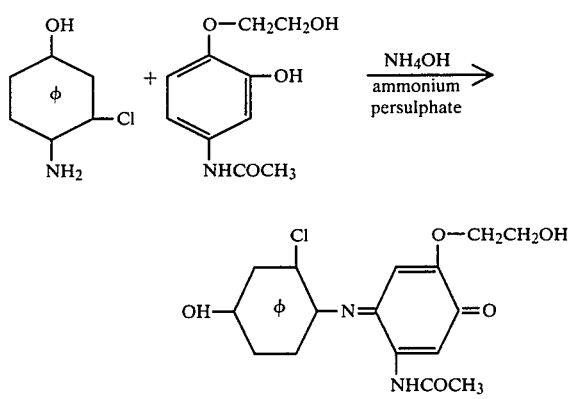

0.05 mole (10.55 g) of (2-hydroxy-4-acetylamino)phenoxyethanol is dissolved in 100 ml of isopropyl alcohol to which 80 ml of 20% strength ammonia has been added. 300 g of crushed ice are added to this alcoholic solution followed by, gradually, simultaneously and with effective stirring, on the one hand, 0.05 mole (7.18 g) of 3-chloro-4-aminophenol dissolved in 100 ml of water to which 6 ml of 35% strength hydrochloric acid have been added and, on the other hand, 0.1 mole (22.8 g) of ammonium persulphate in 100 ml of water. When the addition is complete, a blue solution is obtained which contains the expected indophenol in the form of a phenate. The pH is adjusted to 7.5 with acetic acid. The indophenol precipitates. It is filtered off, washed with water and dried under vacuum. After recrystallization from ethanol, the product melts at 230° C.

Analysis of the product obtained gives the following results:

| ANALYSIS | CALCULATED FOR $C_{16}H_{15}N_2O_5Cl$ | FOUND |
|---|---|---|
| C % | 54.79 | 54.84 |
| H % | 4.31 | 4.37 |
| N % | 7.99 | 7.99 |
| Cl % | 22.81 | 22 72 |
| O % | 10.11 | 10.11–9.99 |

EXAMPLE 6

Preparation of
N-[(4'-hydroxy-2'-chloro)phenyl]-2-amino-5-β-hydroxyethoxy-1,4-benzoquinoneimine

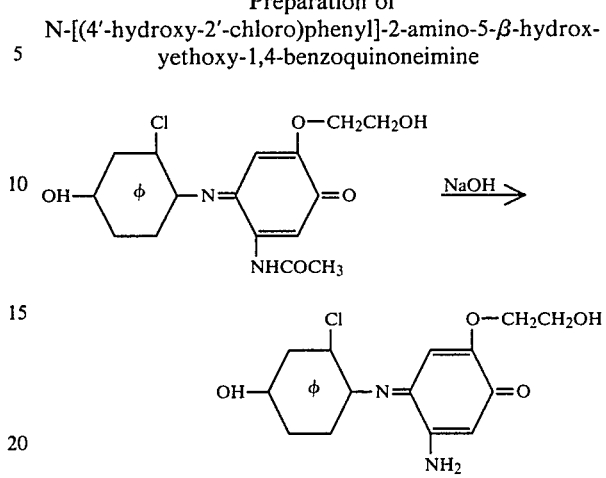

0.0061 mole (2.16 g) of the indophenol obtained by oxidative coupling of 3-chloro-4-aminophenol with (2-hydroxy-4-acetylamino)phenoxyethanol, using the method described earlier, is suspended in 21 ml of an aqueous ethanol solution (60% ethanol/40% water). 21 ml of a normal soda solution are added, with stirring. Dissolution takes place immediately. After stirring for 1 hour at room temperature, the reaction mixture is neutralised with acetic acid. The expected indophenol precipitates. It is filtered off, washed with water and dried under vacuum. After recrystallisation from a mixture of dimethyl sulphoxide and water and drying under vacuum, the product melts at 230° C.

Analysis of the product obtained gives the following results:

| ANALYSIS | CALCULATED FOR $C_{14}H_{13}N_2O_4Cl$ | FOUND |
|---|---|---|
| C % | 54.47 | 54.32 |
| H % | 4.24 | 4.27 |
| N % | 9.07 | 9.13 |
| O % | 20.73 | 20.94 |
| Cl % | 11.48 | 11.38 |

EXAMPLE 7

Preparation of
N-[(4'-hydroxy)phenyl]-2-acetylamino-5-β,γ-dihydroxypropoxy-1,4-benzoquinoneimine

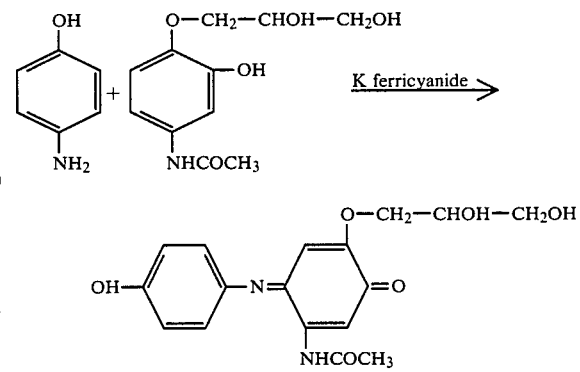

0.03 mole (7.23 g) of 1-(2-hydroxy-4-acetylamino)-phenoxypropane-2,3-diol is added to 50 ml of isopropyl alcohol to which 50 ml of 22°Bé strength ammonia has been added. 0.03 mole (3.27 g) of para-aminophenol and 200 g of crushed ice are added to this suspension with stirring, followed gradually, over 25 min, by 0.12 mole (39.5 g) of potassium ferricyanide dissolved in 120 ml of water. Stirring is continued for a few minutes and then the pH of the reaction mixture is adjusted to 8 with acetic acid to precipitate the expected indophenol. The indophenol is filtered off, washed with water, ethanol, and dried over $P_2O_5$. After recrystallisation from a mixture of dimethyl sulphoxide and water, it melts at 242° C.

Analysis of the product obtained gives the following results:

| ANALYSIS | CALCULATED FOR $C_{21}H_{26}N_4O_6$ | FOUND |
|---|---|---|
| C % | 58.90 | 58.57 |
| H % | 5.20 | 5.24 |
| N % | 8.09 | 8.11 |
| O % | 27.75 | 27.50 |

EXAMPLE 8

Preparation of N-[(4'-N',N'-di-β-hydroxyethylamino)phenyl]-2-acetylamino-5-β-hydroxyethoxy-1,4-benzoquinoneimine

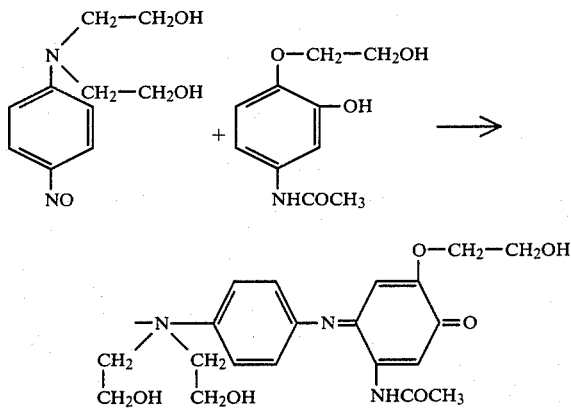

0.008 mole (1.7 g) of 4-nitroso-N,N-di-β-hydroxyethylaniline and 0.01 mole (2.11 g) of 2-hydroxy-4-acetylaminophenoxyethanol are dissolved and this solution is kept stirred for 12 hours under reflux. The indoaniline which has precipitated is filtered off, washed with a little warm alcohol, and dried. After recrystallisation from a mixture of dimethyl sulphoxide and water, the product is dried under vacuum at 50° C. It melts above 260° C.

Molecular weight calculated for $C_{20}H_{25}N_3O_6$: 403.

Molecular weight found by potentiometric assay in acetic acid using an N/10 perchloric acid solution: 403.

Analysis of the product obtained gives the following results:

| ANALYSIS | CALCULATED FOR $C_{20}H_{25}N_3O_6$ | FOUND |
|---|---|---|
| C % | 59.55 | 59.16 |
| H % | 6.20 | 6.29 |
| N % | 10.42 | 10.40 |
| O % | 23.82 | 24.01 |

EXAMPLE 9

Preparation of N-[(4'-N'-ethyl-N'-carbamylmethylamino)-phenyl]-2-ethoxycarbonylamino-5-β-hydroxyethoxy-1,4-benzoquinoneimine

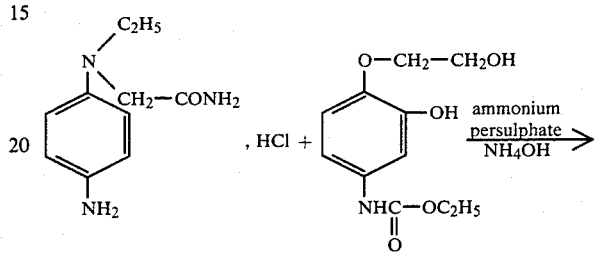

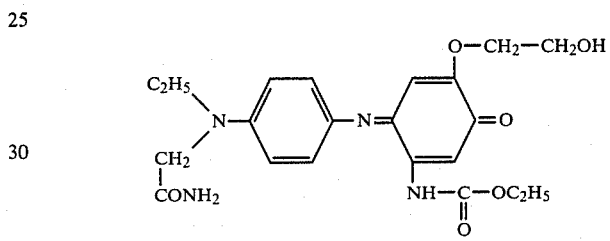

0.03 mole (7.23 g) of (2-hydroxy-4-ethoxycarbonylamino)phenoxyethanol is dissolved in 65 ml of isopropyl alcohol to which 65 ml of 22°Bé strength ammonia have been added. 0.03 mole (6.9 g) of N-ethyl-N-carbamylmethylpara-phenylenediamine hydrochloride, previously dissolved in 50 ml of water, and 200 g of crushed ice, are added to this solution. 0.06 mole (13.7 g) of ammonium persulphate dissolved in 50 ml of water is then added to the reaction mixture dropwise, with stirring, over 20 minutes. Stirring is continued for 15 minutes and then the expected indoaniline, which has precipitated, is filtered off. The product is washed with water, and dried under vacuum at 50° C. After recrystallisation from a mixture of dimethyl sulphoxide and water followed by drying under vacuum at 50° C., the product melts at 130° C.

Molecular weight calculated for $C_{21}H_{26}N_4O_6$: 430.

Molecular weight found by potentiometric assay in acetic acid using perchloric acid: 426.

Analysis of the product obtained gives the following results:

| ANALYSIS | CALCULATED FOR $C_{17}H_{18}N_2O_6$ | FOUND |
|---|---|---|
| C % | 58.60 | 58.40 |
| H % | 6.05 | 6.12 |
| N % | 13.02 | 12.80 |
| O % | 22.33 | 22.60 |

EXAMPLE 10

Preparation of the hydrate of N-[(4'-carbamylethylamino)-phenyl]-2-acetylamino-5-β,γ-dihydroxypropoxy-1,4-benzoquinoneimine

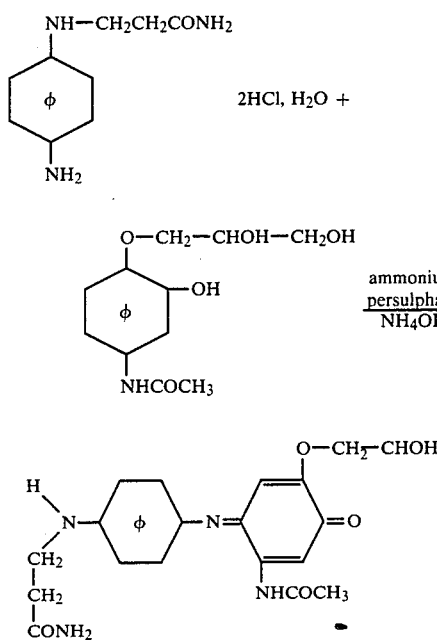

0.02 mole (4.82 g) of 1-(2-hydroxy-4-acetylamino)-phenoxypropane-2,3-diol is added to 40 ml of isopropyl alcohol to which 40 ml of 22°Bé strength ammonia have been added. 140 g of crushed ice are added to this suspension followed by, simultaneously, with stirring, on the one hand, a solution of 0.02 mole (5.4 g) of N-carbamylethylpara-phenylenediamine dihydrochloride monohydrate in 30 ml of water, and, on the other hand, a solution of 0.04 mole (9.12 g) of ammonium persulphate in 30 ml of water. When the additions have been completed, stirring is continued for another 15 minutes and the expected indoaniline, which has precipitated, is then filtered off. It is washed with water and then with alcohol. After recrystallisation from a mixture of dimethyl sulphoxide and water, the product melts between 135° and 137° C.

Molecular weight calculated for $C_{20}H_{24}N_4O_6.H_2O$: 434.

Molecular weight found by potentiometric assay in acetic acid using perchloric acid: 430.

Analysis of the product obtained gives the following results:

| ANALYSIS | CALCULATED FOR $C_{20}H_{26}N_4O_7$ | FOUND |
|---|---|---|
| C % | 55.30 | 54.87 |
| H % | 5.99 | 5.92 |
| N % | 12.90 | 12.86 |
| O % | 25.80 | 26.17 |

EXAMPLE 11

Preparation of the hydrate of N-[(4'-amino-3',5'-dimethyl)-phenyl]-2-acetylamino-5-β,γ-dihydroxypropoxy-1,4-benzoquinoneimine

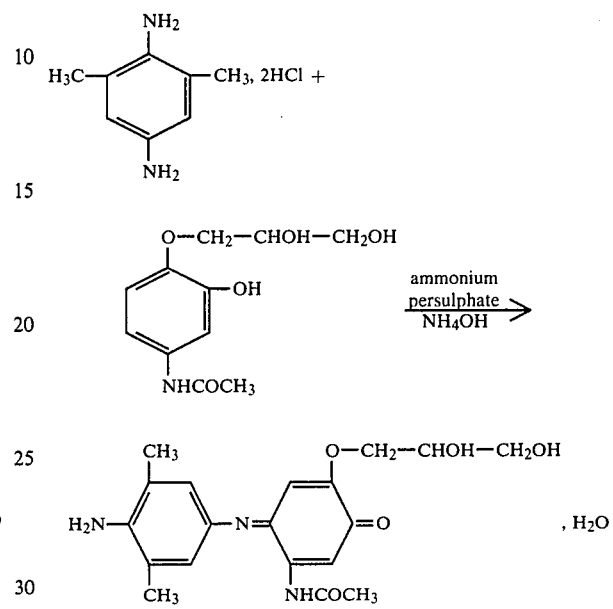

0.02 mole (4.82 g) of 1-(2-hydroxy-4-acetylamino)-phenoxypropane-2,3-diol is added to 40 ml of isopropyl alcohol to which 40 ml of 22°Bé strength ammonia have been added. 140 g of crushed ice are added to this suspension followed by, simultaneously, with stirring, on the one hand, a solution of 0.02 mole (4.18 g) of 2,6-dimethylpara-phenylenediamine dihydrochloride in 30 ml of water and, on the other hand, 0.04 mole (9.12 g) of ammonium persulphate in 30 ml of water. When the additions have been completed, stirring is continued for 2 hours and the expected indoaniline, which has precipitated, is filtered off. The product is washed with water and then recrystallised from ethanol. After another recrystallisation from a mixture of dimethyl sulphoxide and water, and drying under vacuum at 50° C., the product melts at 232° C.

Molecular weight calculated for $C_{19}H_{23}N_3O_5.H_2O$: 391.

Molecular weight found by potentiometric assay in acetic acid using perchloric acid: 386.

Analysis of the product obtained gives the following results:

| ANALYSIS | CALCULATED FOR $C_{19}H_{25}N_3O_6$ | FOUND |
|---|---|---|
| C % | 58.31 | 57.80 |
| H % | 6.39 | 6.19 |
| N % | 10.74 | 10.48 |
| O % | 24.55 | 24.95 |

EXAMPLE 12

Preparation of
N-[(4'-amino-3'-methyl)phenyl]-2-acetylamino-5-β-hydroxyethoxy-1,4-benzoquinoneimine

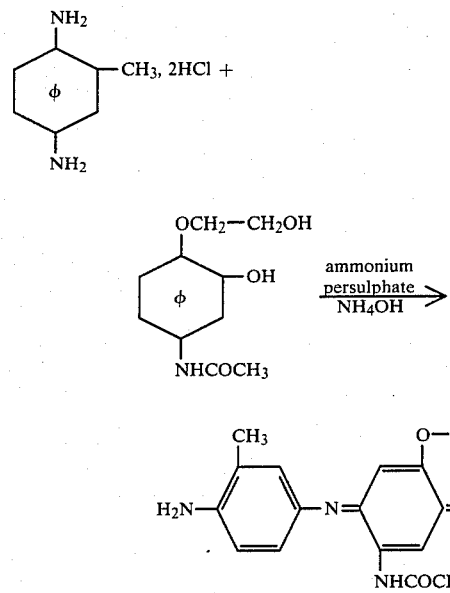

0.06 mole (12.7 g) of (2-hydroxy-4-acetylamino)-phenoxyethanol is added to 130 ml of isopropanol to which 130 ml of 22°Bé strength ammonia have been added. 400 g of crushed ice are added to this solution, followed by, simultaneously, with stirring, on the one hand, a solution of 0.06 mole (11.7 g) of para-diaminotoluene dihydrochloride in 100 ml of water, and, on the other hand, 0.12 mole (27.4 g) of ammonium persulphate in 100 ml of water. when the additions have been completed, stirring is continued for approximately 15 minutes and the indoaniline which has precipitated in a crystalline form is then filtered off. The crude product is washed with acetone and then recrystallised from a mixture of dimethyl sulphoxide and water. After washing with ethanol and drying under vacuum at 50° C., the product melts at 185° C.

Molecular weight calculated for $C_{17}H_{19}N_3O_4$: 329.

Molecular weight found by potentiometric assay in acetic acid using perchloric acid: 324.

Analysis of the product obtained gives the following results.

| ANALYSIS | CALCULATED FOR $C_{17}H_{19}N_3O_4$ | FOUND |
| --- | --- | --- |
| C % | 62.01 | 62.09 |
| H % | 5.77 | 5.74 |
| N % | 12.77 | 12.82 |
| O % | 19.45 | 19.45 |

EXAMPLE 13

Preparation of
N-[(4'-amino-3'-methyl)phenyl]-2-amino-5-hydroxyethoxy-1,4-benzoquinoneimine

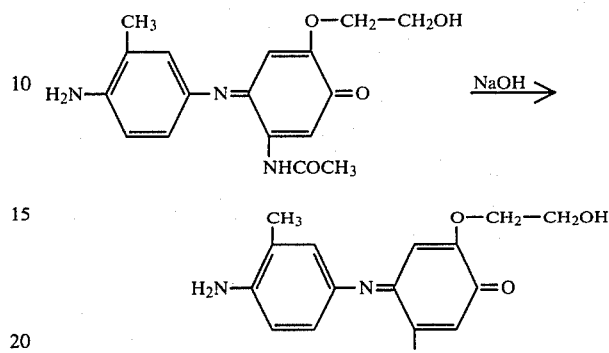

0.012 mole (4 g) of the indoaniline obtained according to the procedure described earlier in Example 12 is suspended in 30 ml of an aqueous ethanol solution (80% ethanol/20% water). 40 ml of normal soda solution are added to this suspension with stirring. The reaction mixture rapidly becomes homogeneous. After stirring for 1 hour, 200 g of ice water are added to the reaction mixture. The expected indoaniline precipitates in the form of a resin which crystallises slowly. It is filtered off, washed with water and dried under vacuum. The melting point is 120° C.

EXAMPLE 14

Preparation of
N-[(4'-amino-3'-chloro)]phenyl-2-acetylamino-5-β,γ-dihydroxypropoxy-1,4-benzoquinoneimine

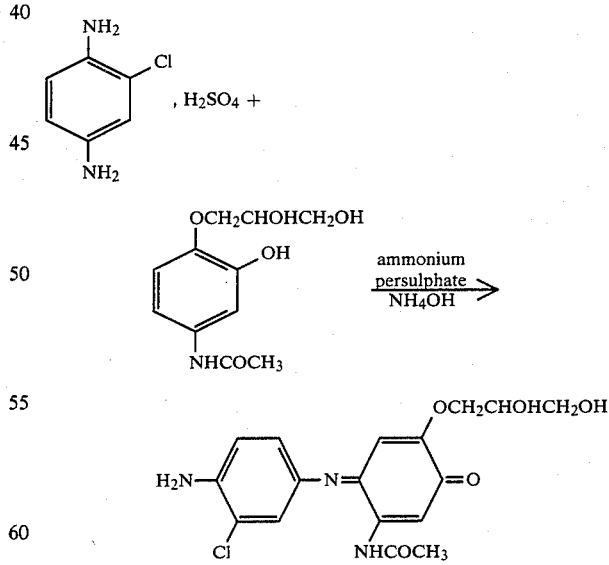

0.02 mole (5.18 g) of 1-(2-hydroxy-4-acetylamino)-phenoxypropane-2,3-diol is added to 40 ml of isopropyl alcohol to which 40 ml of 22°Bé strength ammonia have been added. 140 g of ice are added to this suspension and into this are poured simultaneously, on the one hand, a solution of 0.02 mole (4.81 g) of 2-chloro-1,4- diaminobenzene sulphate in 60 ml of water, to which the quantity of 22°Bé strength ammonia which is required to obtain this solution has been added, and, on the other hand, a solution of 0.04 mole (9.12 g) of ammonium persulphate in 30 ml of water, over 5 minutes. Stirring is continued for 10 minutes, and the expected indoaniline which has precipitated is then filtered off. The product is washed with water.

After recrystallisation from a mixture of water and ethyl alcohol and after being converted back into a paste in boiling water, followed by drying under vacuum at 70° C., the product melts at 226° C.

Molecular weight calculated for $C_{17}H_{18}N_3O_5Cl$: 579.8.

Molecular weight found by potentiometric assay in acetic acid using perchloric acid: 376.

Analysis of the product obtained gives the following results:

| ANALYSIS | CALCULATED FOR $C_{17}H_{18}N_3O_5Cl$ | FOUND |
|---|---|---|
| C % | 53.76 | 53.63 |
| H % | 4.78 | 4.81 |
| N % | 11.06 | 11.13 |
| O % | 21.06 | 21.14 |
| Cl % | 9.33 | 9.41 |

EXAMPLE 15

The following dyeing composition is prepared:

| | |
|---|---|
| N—[(4'-amino)phenyl]-2-acetylamino-5-$\beta$-hydroxyethoxy-1,4-benzoquinoneimine | 0.25 g |
| Ethanol (96°) | 25 g |
| Triethanolamine (2% by weight in aqueous solution) | 0.5 g |
| Water q.s. | 100 g |

The pH of the composition is 8.

This mixture, when applied for 20 min at 28° C. to hair which is bleached white, imparts to it, after rinsing and shampooing, a purple-tinged grey colour.

EXAMPLE 16

The following dyeing composition is prepared:

| | |
|---|---|
| N—[(4'-amino)phenyl]-2-amino-5-$\beta$-hydroxyethoxy-1,4-benzoquinoneimine | 0.41 g |
| 2-Butoxyethanol | 20 g |
| Triethanolamine (1% by weight in aqueous solution) | 0.1 g |
| Water q.s. | 100 g |

The pH of the composition is 6.5.

This solution, when applied for 30 min at 28° C. to hair which has been bleached white, imparts to it, after rinsing and shampooing, a light-red colour.

EXAMPLE 17

The following dyeing composition is prepared:

| | |
|---|---|
| N—[(4'-amino)phenyl]-2-amino-5-$\beta,\gamma$-dihydroxypropoxy-1,4-benzoquinoneimine | 0.82 g |
| Ethanol (96°) | 25 g |
| Triethanolamine (2% by weight in aqueous solution) | 0.1 g |
| Water q.s. | 100 g |

The pH of the composition is 7.8.

This mixture, when applied for 20 min at 28° C. to hair which has been bleached white imparts to it, after rinsing and shampooing, a purple light-red colour.

EXAMPLE 18

The following dyeing composition is prepared:

| | |
|---|---|
| N—[(4'-amino)phenyl]-2-acetylamino-5-$\beta,\gamma$-dihydroxypropoxy-1,4-benzoquinoneimine | 0.15 g |
| 50% solution in ethanol of a quaternary copolymer of polyvinylpyrrolidone (average molecular weight: 100,000), sold by the company "GENERAL ANILIN FRANCE" under the name of "GAFQUAT 734" | 2 g |
| Isopropyl alcohol | 20 g |
| Triethanolamine (20% by weight in aqueous solution) | 0.1 g |
| Water q.s. | 100 g |

The pH of the composition is 8.

This solution, when applied as a hair-setting lotion to hair which has been bleached white, imparts to it, after drying, a wistaria-like colour.

EXAMPLE 19

The following dyeing composition is prepared:

| | |
|---|---|
| N—[(4'-hydroxy-2'-chloro)phenyl]-2-acetyl-amino-5-$\beta$-hydroxyethoxy-1,4-benzoquinoneimine | 0.38 g |
| 2-Butoxyethanol | 25 g |
| Triethanolamine (2% by weight in aqueous solution) | 0.5 g |
| Water q.s. | 100 g |

The pH of the composition is 7.

This mixture, when applied for 30 min at 28° C. to hair which has been bleached white, imparts to it, after rinsing and shampooing, a pink champagne colour.

EXAMPLE 20

The following dyeing composition is prepared:

| | |
|---|---|
| N—[(4'-hydroxy-2'-chloro)phenyl]-2-amino-5-$\beta$-hydroxyethoxy-1,4-benzoquinoneimine | 0.33 g |
| Ethanol (96°) | 10 g |
| Cetyl-stearyl alcohol sold under the name "ALFOL C16/18 E" by the company | |
| Ammonia (22° Be) | 0.05 g |
| Water q.s. | 100 g |

The pH of the composition is 8.3.

This mixture, when applied for 30 min at 30° C. to hair which has been bleached white, imparts to it, after rinsing and shampooing, a golden blonde colour.

EXAMPLE 21

The following dyeing composition is prepared:

| | |
|---|---|
| N—[(4'-amino-3',5'-dimethyl)phenyl]-2-acetylamino-5-$\beta,\gamma$-dihydroxypropoxy-1,4-benzoquinoneimine hydrate | 0.205 g |
| Hydroxyethylcellulose | 2 g |
| Ethanol (96°) | 20 g |
| Aqueous solution of triethanolamine, 1% by weight | 0.1 g |
| Water q.s. | 100 g |

The pH of the composition is 7.2.

This mixture, when applied for 25 min at 28° C. to bleached hair, imparts to it, after rinsing and shampooing, a silvery light-blue colour.

EXAMPLE 22

The following hair-setting lotion is prepared:

| | |
|---|---|
| N—[(4'-N',N'—di-$\beta$-hydroxyethylamino)-phenyl]-2-acetylamino-5-$\beta$-hydroxyethoxy-1,4-benzoquinoneimine | 0.18 g |
| 90% vinyl acetate/10% crotonic acid copolymer sold by the company "NATIONAL | |

EXAMPLE 22

The following hair-setting lotion is prepared:

| | |
|---|---|
| N—[(4'-N'—ethyl-N'—carbamylmethylamino)-phenyl]-2-ethoxycarbonylamino-5-$\beta$-hydroxyethoxy-1,4-benzoquinoneimine | 0.1 g |
| 90% vinyl acetate/10% crotonic acid copolymer sold by the company "NATIONAL STARCH" under the name of "RESYN 28-1310" | 1.5 g |
| Ethanol (96°) | 50 g |
| Ammonia (5% strength) | 1.5 g |
| Water q.s. | 100 g |

The pH of the lotion is 6.2.

This solution, when applied as a hair-setting lotion to bleached hair, imparts to it a silvery mauve shade.

EXAMPLE 23

The following hair-setting lotion is prepared:

| | |
|---|---|
| N—[(4'-N',N'—di-$\beta$-hydroxyethylamino)-phenyl]-2-acetylamino-5-$\beta$-hydroxyethoxy-1,4-benzoquinoneimine | 0.105 g |
| N—[(4'-hydroxy)phenyl]-2-$\beta$-hydroxyethyl-amino-5-methyl-1,4-benzoquinoneimine | 0.15 g |
| Quaternary copolymer of polyvinylpyrrolidone (50% strength solution in ethanol - mean MW 100,000), sold under the name "GAFQUAT 734" by the company "GENERAL ANILIN FRANCE" | 2 g |
| Isopropyl alcohol | 20 g |
| Aqueous solution of triethanolamine, 20% strength | 0.15 g |
| Water q.s. | 100 g |

The pH of the lotion is 8.0.

This solution, when applied as a hair-setting lotion to bleached hair, imparts to it a golden honey colour.

EXAMPLE 24

The following dyeing composition is prepared:

| | |
|---|---|
| N—[(4'-hydroxy)phenyl]-2-acetylamino-5-$\beta$,$\gamma$-dihydroxypropoxy-1,4-benzoquinoneimine | 0.2 g |
| N—[(4'-amino-3',5'-dimethyl)phenyl]-2-acetylamino-5-$\beta$,$\gamma$-dihydroxypropoxy-1,4-benzoquinoneimine | 0.08 g |
| 2-Butoxyethanol | 25 g |
| Aqueous solution of triethanolamine, 2% by weight | 1.5 g |
| Water q.s. | 100 g |

The pH of the composition is 8.2.

This mixture, when applied for 25 min at 28° C. to bleached hair, imparts to it, after rinsing and shampooing, a pearly sand colour.

EXAMPLE 25

The following hair-setting lotion is prepared:

| | |
|---|---|
| N—[(4-N'-carbamylethylamino)phenyl]-2-acetylamino-5-$\beta$,$\gamma$-dihydroxypropoxy-1,4-benzoquinoneimine hydrate | 0.03 g |
| N—[(4'-hydroxy)-phenyl]-2-acetylamino-5-$\beta$,$\gamma$-dihydroxypropoxy-1,4-benzoquinoneimine | 0.1 g |
| 90% vinyl acetate/10% crotonic acid copolymer, sold by the company "NATIONAL STARCH" under the name of "RESYN 281310" | 1.5 g |
| Ethanol (96°) | 50 g |
| Aqueous solution of triethanolamine, 20% by weight | 1.8 g |
| Water q.s. | 100 g |

The pH of the lotion is 7.8.

This solution, when applied as a hair-setting lotion to bleached hair, imparts to it a pearly pink beige colour.

EXAMPLE 26

The following hair-setting lotion is prepared:

| | |
|---|---|
| N—[(4'-hydroxy)phenyl]-2-acetylamino-5-$\beta$,$\gamma$-dihydroxypropoxy-1,4-benzoquinoneimine | 0.15 g |
| 90% vinyl acetate/10% crotonic acid copolymer, sold by the company "NATIONAL STARCH" under the name of "RESYN 281310" | 1.5 g |
| Ethanol (96°) | 50 g |
| Aqueous solution of triethanolamine, 20% strength | 2 g |
| Water q.s. | 100 g |

The pH of the composition is 7.8.

This solution, when applied as a hair-setting lotion to bleached hair, imparts to it an apricot-coloured shade.

EXAMPLE 27

The following dyeing composition is prepared:

| | |
|---|---|
| N—[(4'-amino-3'-methyl)phenyl]-2-acetyl-amino-5-$\beta$-hydroxyethoxy-1,4-benzoquinoneimine | 0.1 g |
| Cetyl-stearyl alcohol sold under the name "ALFOL C16/18 E" by the company "CONDEA" | 8 g |
| Cetyl-stearyl sodium sulphate sold under the name "CIRE DE LANETTE E" by the company "HENKEL" | 0.5 g |
| Ethoxylated castor oil sold under the name "CEMULSOL B" by the company "RHONE POULENC | 1 g |
| Oleic diethanolamide | 1.5 g |
| 2-Butoxyethanol | 10 g |
| Water q.s. | 100 g |

The pH of the composition is 7.5.

This dyeing composition, when applied for 20 min at 28° C. to hair which has been bleached white, imparts to it, after rinsing and shampooing, a silver-grey colour with mauve sheen.

EXAMPLE 28

The following hair-setting lotion is prepared:

| | |
|---|---|
| N—[(4'-amino-3'-methyl)phenyl]-2-acetyl-amino 5-$\beta$-hydroxyethoxy-1,4-benzoquinoneimine | 0.2 g |
| 90% vinyl acetate/10% crotonic acid copolymer, sold by the company "NATIONAL STARCH" under the name of "RESYN 281310" | 1.6 g |
| Ethanol (96°) | 50 g |
| 20% strength triethanolamine solution | 1.1 g |

-continued

| | |
|---|---|
| Water q.s. | 100 g |

The pH of the lotion is 7.5.

This solution, when applied as a hair-setting lotion to bleached hair, imparts to it a silvery wistaria-like colour.

EXAMPLE 29

The following dyeing composition is prepared:

| | |
|---|---|
| N—[(4'-amino-3'-methyl)phenyl]-2-amino-5-β-hydroxyethoxy-1,4-benzoquinoneimine | 0.5 g |
| Hydroxyethylcellulose | 2 g |
| 2-Butoxyethanol | 10 g |
| 1% strength triethanolamine solution | 0.1 g |
| Water q.s. | 100 g |

The pH of the composition is 8.2.

This dyeing composition, when applied for 25 min at 28° C. to hair which is 95% naturally white, imparts to it, after rinsing and shampooing, a purple-red light chestnut colour.

EXAMPLE 30

The following dyeing composition is prepared:

| | |
|---|---|
| N—[(4'-amino)phenyl]-2-amino-5-β-hydroxyethoxy-1,4-benzoquinoneimine | 0.4 g |
| N—[(4'-amino)phenyl]-2-acetylamino-5-β-hydroxyethoxy-1,4-benzoquinoneimine | 0.1 g |
| N—[(4'-hydroxy-2'-chloro)phenyl]-2-amino-5-hydroxyethoxy-1,4-benzoquinoneimine | 0.3 g |
| 3-Nitro-4-N'—β-hydroxyethylamino-N,N—di-β-hydroxyethylaniline | 0.05 g |
| 3-Nitro-5-N—β-hydroxyethylaminoanisole | 0.02 g |
| Hydroxyethylcellulose | 2 g |
| 2-Butoxyethanol | 10 g |
| 1% strength triethanolamine solution | 0.15 g |
| Water q.s. | 100 g |

The pH of the composition is 8.1.

This dyeing composition, when applied for 30 min at 30° C. to hair which is 90% naturally white, imparts to it, after rinsing and shampooing, a coppery light chestnut colour.

EXAMPLE 31

The following hair-setting lotion is prepared:

| | |
|---|---|
| N—[(4'-amino-3'-chloro)phenyl]-2-acetylamino-5-β,γ-dihydroxypropoxy-1,4-benzoquinoneimine | 0.08 g |
| Ethanol (96°) | 50 g |
| Vinyl acetate/crotonic acid copolymer (90/10) | 1.6 g |
| Triethanolamine (1% by weight in aqueous solution) | 0.5 g |
| Water q.s. | 100 g |

The pH of the lotion is 5.3.

This solution, when applied as a hair-setting lotion to bleached hair, imparts to it a slivery light Parma shade.

We claim:

1. A compound of formula:

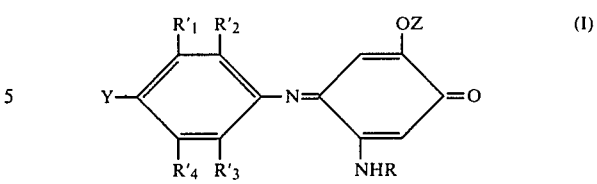

wherein Z represents a monohydroxylated or polyhydroxylated hydrocarbon radical, of 1 to 6 carbon atoms, or an aminoalkyl radical of formula:

wherein n is an integer from 1 to 6 and $R_1$ and $R_2$, which are identical or different, represent a hydrogen atom or an alkyl, hydroxyalkyl or acyl radical of 1 to 4 carbon atoms; R represents a hydrogen atom or an alkyl, hydroxyalkyl, polyhydroxyalkyl, monocarbamylalkyl, dicarbamylalkyl, aminoalkyl, acyl, alkoxycarbonyl, carbamyl or monoalkylcarbamyl radical of 1 to 6 carbon atoms; $R'_1$, $R'_2$, $R'_3$ and $R'_4$, which are identical or different, represent a hydrogen atom, a halogen atom or an alkyl, hydroxyalkyl, alkoxy or hydroxyalkoxy radical, of 1 to 6 carbon atoms; and Y represents OH or $NR'_5R'_6$, wherein $R'_5$ and $R'_6$, which are identical or different, represent a hydrogen atom or an alkyl, monohydroxyalkyl, polyhydroxyalkyl, carbamylalkyl, mesylaminoalkyl or methoxyalkyl radical of 1 to 6 carbon atoms.

2. A compound according to claim 1, wherein Z is a —CH$_2$CH$_2$OH, —CH$_2$—CHOH—CH$_2$OH, —CH$_2$—CHOH—CH$_3$, —CH$_2$—CH$_2$NH$_2$, —CH$_2$—CH$_2$—NHCH$_3$, —CH$_2$—CH$_2$—NHCOCH$_3$ or

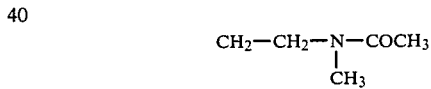

radical.

3. A compound according to claim 1 wherein R is a formyl, acetyl or propionyl radical or a hydrogen atom.

4. A colouring composition for hair, comprising a cosmetic base and at least one compound as claimed in claim 1.

5. A composition according to claim 4, wherein the compound as claimed in claim 1, is present in the composition in an amount of from 0.01 to 2% by weight relative to the total weight of the composition.

6. A composition according to claim 4, which has a pH from 6 to 8.5.

7. A composition according to claim 4, which contains at least one alkalising agent which is ammonia, an alkylamine, an alkanolamine, an alkylalkanolamine, sodium or potassium hydroxide, or sodium, potassium or ammonium carbonate.

8. A colouring hair-setting lotion according to claim 6 which contains a cosmetic resin in an aqueous-alcoholic carrier.

9. A composition according to claim 8, wherein the aqueous-alcoholic carrier comprises from 10 to 70% by weight of alcohol and from 0.5 to 4% by weight of cosmetic resin.

10. A composition for dyeing hair according to claim 4, in the form of liquid, cream, gel or aerosol.

11. N-[(4'-amino)phenyl]-2-amino-5-β-hydroxyethoxy-1,4-benzoquinoneimine.

12. A compound of the formula

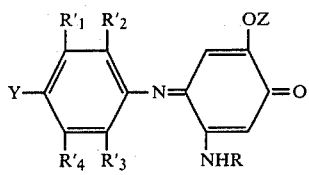

wherein

Z represents —CH$_2$CH$_2$OH or —CH$_2$CHOHCH$_2$OH,

R represents hydrogen, —COCH$_3$ or

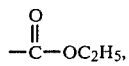

R'$_1$, R'$_2$, R'$_3$ and R'$_4$ each independently represent hydrogen, methyl or chlorine, and Y represents NH$_2$, OH,

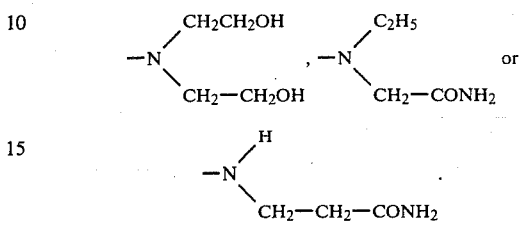

13. N-[(4'-amino-3'-methyl)phenyl]-2-amino-5-hydroxyethoxy-1,4-benzoquinoneimine.

* * * * *